United States Patent
Hessefort et al.

(10) Patent No.: US 7,008,618 B1
(45) Date of Patent: Mar. 7, 2006

(54) WATER SOLUBLE MONOMERS AND POLYMERS FOR PROTECTING SUBSTRATES FROM ULTRAVIOLET LIGHT

(75) Inventors: Yin Z. Hessefort, Naperville, IL (US); John D. Morris, Naperville, IL (US); Wayne M. Carlson, Batavia, IL (US); Mingli Wei, Naperville, IL (US); Murat Quadir, Naperville, IL (US); Larry E. Brammer, Jr., Aurora, IL (US)

(73) Assignee: Nalco Company, Naperville, IL (US)

( * ) Notice: Subject to any disclaimer, the term of this patent is extended or adjusted under 35 U.S.C. 154(b) by 69 days.

(21) Appl. No.: 10/290,978

(22) Filed: Nov. 8, 2002

(51) Int. Cl.
*A61K 7/06* (2006.01)
*A61K 31/74* (2006.01)
*A61K 7/42* (2006.01)
*A61K 7/44* (2006.01)
*A61K 7/00* (2006.01)

(52) U.S. Cl. .............. 424/70.1; 424/78.02; 424/78.08; 424/59; 424/60; 424/400; 424/401

(58) Field of Classification Search .............. 424/70.1, 424/78.02, 78.08, 400, 401, 59, 60
See application file for complete search history.

(56) References Cited

U.S. PATENT DOCUMENTS

| | | |
|---|---|---|
| 3,864,473 A | 2/1975 | Ciaudelli |
| 4,166,109 A | 8/1979 | Jacquet et al. |
| 4,201,766 A | 5/1980 | Grollier et al. |
| 4,233,430 A | 11/1980 | Jacquet et al. |
| 5,134,223 A | 7/1992 | Langer et al. |
| 5,243,021 A * | 9/1993 | Langer et al. ............ 528/272 |
| 5,250,652 A * | 10/1993 | Langer et al. ............ 528/125 |
| 5,601,811 A | 2/1997 | Gallagher et al. |
| 5,633,403 A | 5/1997 | Gallagher et al. |
| 5,843,410 A | 12/1998 | Kim et al. |
| 5,922,310 A | 7/1999 | Chaudhuri et al. |
| 6,045,586 A | 4/2000 | Bacher et al. |
| 6,207,740 B1 | 3/2001 | Zhao et al. |
| 6,464,817 B1 | 10/2002 | Olson et al. |

* cited by examiner

*Primary Examiner*—Shelley A. Dodson
(74) *Attorney, Agent, or Firm*—Michael B. Martin; Thomas M. Breininger

(57) ABSTRACT

A UV-protective composition for treating substrates comprising one or more water-soluble, cationic, UV-absorbing polymers, wherein the cationic, UV-absorbing polymers are prepared by polymerizing one or more vinyl, allyl or acrylic monomers with one or more vinyl or acrylic monomers that absorb ultraviolet light radiation having a wavelength of about 200 to about 420 nm and a method of treating substrates.

19 Claims, No Drawings

WATER SOLUBLE MONOMERS AND POLYMERS FOR PROTECTING SUBSTRATES FROM ULTRAVIOLET LIGHT

TECHNICAL FIELD

This invention concerns a composition and method for protecting substrates from ultraviolet radiation. More particularly, this invention concerns a composition comprising water soluble, cationic, UV-absorbing polymers and methods of using the composition.

BACKGROUND OF THE INVENTION

Ultraviolet (UV) light radiation is known to be a factor that damages paints and other protective or decorative coatings, plastics, various textiles made from natural and manmade fibers and keratin substrates including human skin and hair. Damage to human skin, for example, can include loss of skin elasticity and the appearance of wrinkles, erythema and skin burning and the inducement of phototoxic or photoallergic reactions. Hair damage by UV light is perceived as dryness, reduced strength, rough surface texture, loss of color and luster, stiffness and brittleness.

In the case of plastics, UV exposure can result in loss of tensile strength, embrittlement and discoloration. UV exposure can also result in fading of painted surfaces or dyed textiles. To help prevent such degradation, ultraviolet light stabilizers are often incorporated into a polymer composition, which is used as a protective top layer for underlying materials.

Protection of exposed skin and hair from UV exposure can be effected by applying directly to the skin and hair a preparation containing a UV-absorbing moiety.

Generally, sunscreens for application to the hair require substantivity(adhesion) to the hair, and compatibility in hair care formulations which are often water-based.

Many sunscreen agents, however, do not fully meet these requirements. Thus the level of sunscreen agents that could be incorporated into hair care formulations and/or the level of sunscreen agents that can deposit on the hair are limited. Accordingly, there is an ongoing need for new sunscreen agents with improved substantivity and water solubility for incorporation into aqueous formulations.

Skin and hair can also be protected by covering with clothing, thereby avoiding direct exposure of the skin and hair to sunlight. However, most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer. Therefore, there is also a need to provide protection against UV radiation for skin which lies underneath clothing, including lightweight summer clothing, which is undyed or dyed only in pale shades.

Commonly used UV absorbers such as benzotriazoles and benzophenone are highly effective in their UV absorber capacity. However, they are quite costly and can prove difficult to incorporate within different target media. Furthermore, UV absorbers of this type present handling difficulties in that they are generally produced and utilized in powder form and have relatively low melting points. A liquid, on the other hand, is much easier to handle, does not require melting, and provides more effective and thorough mixing throughout the target material.

Thus, there exists a continuing need for effective liquid UV absorbing compositions which exhibit sufficient versatility to be incorporated within or applied to different and various media and substrates.

SUMMARY OF THE INVENTION

This invention is a composition for protecting a substrate from the effect of ultraviolet light comprising about 0.1 to about 10 weight percent, based on polymer actives, of one or more water-soluble, cationic, ultraviolet light absorbing polymers, wherein the cationic, ultraviolet light absorbing polymers are prepared by polymerizing one or more vinyl, allyl or acrylic monomers with one or more vinyl or acrylic monomers that absorb ultraviolet light radiation having a wavelength of about 200 to about 420 nm.

This invention is also a method of protecting a substrate from the effects of ultraviolet light comprising applying to the substrate an effective ultraviolet light protective amount of a composition comprising about 0.1 to about 10 weight percent, based on polymer actives, of one or more water-soluble, cationic, ultraviolet light absorbing polymers, wherein the cationic, ultraviolet light absorbing polymers are prepared by polymerizing one or more vinyl, allyl or acrylic monomers with one or more vinyl or acrylic monomers that absorb ultraviolet light radiation having a wavelength of about 200 to about 420 nm.

The polymers of this invention are water soluble and contain cationic moieties to improve substantivity. The cationic portion of the polymer also gives the polymer a 'multi-functional' nature in that it offers hair and skin conditioning advantages.

A further advantage of the current invention is that the polymer can alternately contain anionic and/or ampholytic (or amphoteric) characteristics. This will improve the polymer's performance in conditioning, dye retention, etc.

DETAILED DESCRIPTION OF THE INVENTION

The water soluble UV-absorbing polymers of this invention can be synthesized using methods known in the art for free radical polymerization in an aqueous medium, including water-in-oil polymerization methods, dispersion polymerization methods or solution polymerization methods.

The preparation of water-in-oil emulsion polymers has been described in, for example, U.S. Pat. No. 2,982,749; 3,284,393; and U.S. Pat. No. 3,734,873. See also Hunkeler et al., "Mechanism, Kinetics and Modeling of the Inverse-Microsuspension Homopolymerization of Acrylamide", Polymer (1989), 30(1), 127–42; and Hunkeler et al., "Mechanism, Kinetics and Modeling of Inverse-Microsuspension Polymerization: 2. Copolymerization of Acrylamide with Quaternary Ammonium Cationic Monomers", Polymer (1991), 32(14), 2626–40.

A general procedure for the manufacture of water-in-oil emulsion polymers containing UV-absorbing monomers is as follows. The types and quantities of specific components in the formula (monomers, initiators, Chain Transfer Agents, for example) will vary depending upon the polymer that is being synthesized.

An aqueous phase is prepared by mixing together in water one or more UV-absorbing monomers and any additional water soluble monomers, and different polymerization additives such as inorganic salts, chelants, pH buffers, chain transfer agents and branching or cross-linking agents.

An organic phase is prepared by mixing together an inert hydrocarbon liquid with one or more oil soluble surfactants. The surfactant mixture should have a low HLB, to ensure the formation of an oil continuous emulsion. Appropriate surfactants for water-in-oil emulsion polymerizations, which are commercially available, are compiled in the North American Edition of McCutcheon's Emulsifiers & Detergents. The oil phase may need to be heated to ensure the formation of a homogeneous oil solution.

The oil phase is charged into a reactor equipped with a mixer, a thermocouple, a nitrogen purge tube, and a condenser. Adding the aqueous phase to the reactor containing the oil phase with vigorous stirring forms an emulsion. The resulting emulsion is heated to the desired temperature, purged with nitrogen, and a free-radical initiator is added. The reaction mixture is stirred for several hours under a nitrogen atmosphere at the desired temperature. Upon completion of the reaction, the water-in-oil emulsion polymer is cooled to room temperature, where any desired post-polymerization additives, such as antioxidants, or a high HLB surfactant (as described in U.S. Pat. No. 3,734, 873) may be added.

The resulting emulsion polymer is a free-flowing liquid. An aqueous solution of the water-in-oil emulsion polymer can be generated by adding a desired amount of the emulsion polymer to water with vigorous mixing in the presence of a high-HLB surfactant (as described in U.S. Pat. No. 3,734, 873).

The preparation of dispersion polymers has been described in, for example U.S. Pat. Nos. 4,929,655; 5,006, 590; 5,597,859; and 5,597,858 and European Patent Nos. 657,478; and 630,909.

A general procedure for the manufacture of dispersion polymers containing UV-absorbing monomers is as follows. The types and quantities of specific components in the formula (salts and stabilizer polymers, for example) will vary depending upon the particular polymer that is being synthesized.

An aqueous solution containing one or more inorganic salts, one or more UV-absorbing monomers and any additional water-soluble monomers, any polymerization additives such as chelants, pH buffers, chain transfer agents, branching or cross-linking agents and one or more water-soluble stabilizer polymers is charged to a reactor equipped with a mixer, a thermocouple, a nitrogen purging tube, and a water condenser.

The monomer solution is mixed vigorously, heated to the desired temperature, and then a water-soluble initiator is added. The solution is purged with nitrogen while maintaining temperature and mixing for several hours. After this time, the products are cooled to room temperature, and any post-polymerization additives are charged to the reactor. Water continuous dispersions of water-soluble polymers are free flowing liquids with product viscosities generally 100–10,000 cP, measured at low shear. Thus, in order to prepare the UV-absorbing polymers as dispersions.

A general procedure for the manufacture of solution polymers is provided to illustrate the preparation of the solution polymers comprising the UV-absorbing monomers described herein.

Two typical processes are described. In the first process, one or more monomers are added to a vessel followed by neutralization with a suitable base. The UV-absorbing monomer can then be added to this monomer solution either with or without prior neutralization or alternatively. Water is then added to the reaction vessel, which is then heated and purged. Polymerization catalysts may also be added to the vessel initially or fed in gradually during the course of the reaction. Water soluble polymerization initiators such as any azo or redox initiator or combination thereof are added along with the monomer solution to the reaction mixture in separate feeds over the same amount of time, usually 2 to 6 hours. The reaction temperature is maintained at about 60–70° C. Additional initiator may be used after addition is complete to reduce residual monomer levels.

The second process involves a one pot adiabatic reaction. An aqueous solution containing one or more water-soluble monomers, any polymerization additives such as chelants, chain transfer agents, branching or cross-linking agents are added to a vacuum sealed glass vessel. The monomer solution is neutralized with a suitable base then purged, and heated between 30 to 60° C. Polymerization catalysts initiators such as any azo or redox initiator or combination thereof are then added to the vessel. Additional initiators may be used after the polymerization is complete to reduce residual monomer levels.

In a preferred aspect of this invention, the UV-absorbing polymers are composed of:
i) about 0.001 to about 60 mole percent of monomer A: one or more vinyl or acrylic monomers that absorb ultraviolet light radiation having a wavelength of about 200 to about 420 nm
ii) 0 to about 99.999 mole percent of monomer B;
iii) 0 to about 99.999 mole percent of monomer C; and
iv) 0 to about 99.999 mole percent of monomer D,
wherein
monomer A is selected from the group consisting of vinyl and acrylic monomers that absorb ultraviolet light radiation having a wavelength of about 200 to about 420 nm;
monomers B and C are selected from the group consisting of acrylic acid and salts thereof, methacrylic acid and salts thereof, maleic acid and salts thereof, maleic anhydride, acrylamide, crotonic acid, acrylamidomethyl propane sulfonic acid and salts thereof; and
monomer D is selected from the group consisting of acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethyl propane sulfonic acid and the sodium salt thereof, vinyl alcohol, vinyl acetate, and N-vinylpyrrolidone, provided that B, C and D are not the same.

In another preferred aspect, the UV-absorbing polymer has a molecular weight of about 10,000 to about 10,000,000.

In another preferred aspect, the UV-absorbing polymer has a molecular weight of about 200,000 to about 2,000,000.

In another preferred aspect, monomer A is selected from the group consisting of

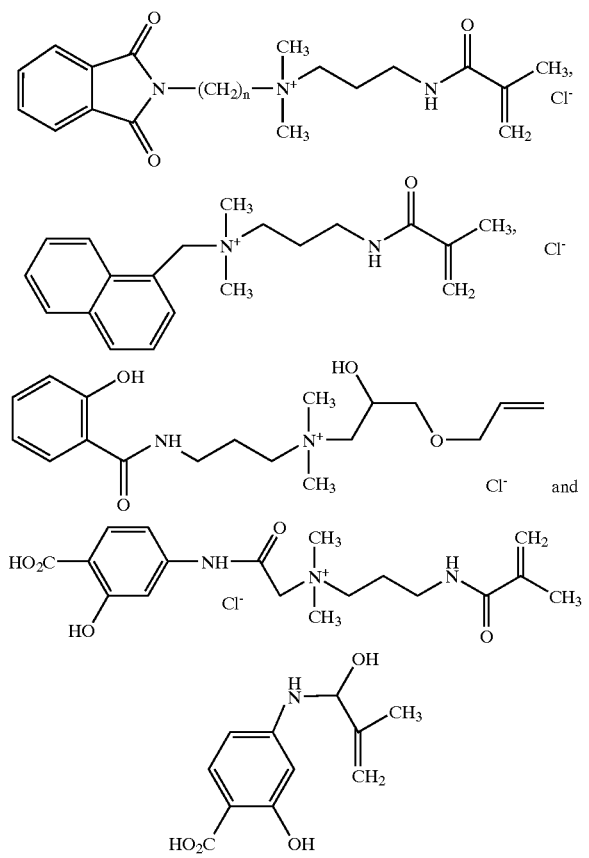

wherein n is 2 or 3.

In another preferred aspect, the UV-absorbing polymer absorbs ultraviolet light radiation having a wavelength of about 290 to about 320 nm.

In another preferred aspect, monomers B and C are selected from the group consisting of acrylamide, methacrylic acid, acrylic acid and acrylamidomethyl propane sulfonic acid and monomer D is selected from the group consisting of methacrylamidopropyl trimethylammonium chloride, acrylamidopropyl trimethylammonium chloride, N-vinylpyrrolidinone, dimethylaminopropyl methacrylamide, dimethylaminopropyl acrylamide, diallyldimethylammonium chloride, dimethylaminoethyl acrylate and dimethylaminoethyl methacrylate.

In another preferred aspect, the UV-absorbing polymer comprises about 0.01 to about 50 mole percent of monomer A.

In another preferred aspect, monomer B is acrylamide; monomer C is acrylic acid; and monomer D is selected from the group consisting of methacrylamidopropyl trimethylammonium chloride, N-vinylpyrrolidinone and diallyldimethylammonium chloride.

In one preferred aspect of this invention, the UV-absorbing polymer is blended with one or more cosmetically acceptable excipients to prepare a composition for applying to keratin substrates including hair, skin and nails.

"Cosmetically acceptable excipient" means a non-toxic, non-irritating substance which when mixed with the UV-absorbing polymer of this invention makes the polymer more suitable to be applied to skin or hair.

In a preferred aspect of this invention, the composition for applying to keratin substrates comprises about 1 to about 3 weight percent, based on polymer actives, of the UV-absorbing polymers.

In another preferred aspect, the excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquatemium-4, polyquatemium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, NY pp. 578–611 (1994) which is incorporated entirely by reference. Complex carbohydrates found in Kirk-Othmer *Encyclopedia of Chemical Technology*, Fourth Edition, Vol. 4, John Wiley and Sons, NY pp. 930–948, 1995 which is herein incorporated by reference.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, trlethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, cocotrimonium chloride, cethethyldimonium bromide, dibehenyldimonium chloride, dihydrogenated tallow benzylmonium chloride, disoyadimonium chloride, ditallowdimonium chloride, hydroxycetyl hydroxyethyl dimonium chloride, hydroxyethyl behenamidopropyl dimonium chloride, hydroxyethyl cetyldimonium chloride, hydroxyethyl tallowdimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quatemium-18, lauralkonium chloride, olealkmonium chloride, cetylpyridinium chloride, Polyquatemium-5, Polyquaternium-6, Polyquaternium-7, Polyquatemium-10, Polyquatemium-22, Polyquatemium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41–42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30–45 alkyl methicone, known as AMS-C30 wax, and stearoxytrimethylsilane (and) stearyl alcohol, known as 580 Wax, each available from Dow Corning®, Midland, Mich., USA. Additonal alkyl and phenyl silicones may be employed to enhance moisturizing properties. Resins such as dimethicone (and) trimethylsoiloxysilicate, known as Dow Corning® 593 or Cyclomethicone (and) Trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethylhexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the tradename Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the tradenames Dow Corning® 244 fluid, Dow Corning® 245 fluid, Dow Corning® 246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2–8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquatemium-28, Polyquatemium-32, Polyquaternium-33, Polyquaternium-36, Polyquaternium-37, Polyquatemium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10–30 Alkyl Acrylate Crosspolymer, such as the Carbopol® and Pemulen® series, both available from B.F. Goodrich, Akron, Ohio, USA; anionic acrylate polymers such as Salcare® AST and cationic acrylate polymers such as Salcare® SC96, available from Ciba Specialties, High Point, N.C., USA; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28, available from International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1–2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD®, Ondeo Nalco Company, Naperville, Ill., USA), benzyl alcohol, imidazolidinyl urea, 1,3-bis (hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

In another preferred aspect, the cosmetically acceptable composition is selected from the group consisting of shampoos, aftershaves, sunscreens, lotions, hand and body creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

Compositions for treating skin include leave-on or rinse-off skin care products such as lotions, hand/body creams, shaving gels or shaving creams, body washes, sunscreens, liquid soaps, deodorants, anti-perspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573, 709 provides a list of non-volatile silicone conditioning agents that can be used in shampoos. The conditioning polymers for use with the present invention are listed in the Cosmetic, Toiletries and Fragrance Associations (CTFA) dictionary. Specific examples nclude the Polyquatemiums (example Polyquatemium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylic acid thickeners available from B.F. Goodrich; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquatemium-1, polyquatemium-2, polyquatemium-4, polyquatemium-5, polyquaternium-6, polyquatemium-7, polyquatemium-8, polyquatemium-9, polyquatemium-10, polyquaternium-11, polyquatemium-12, polyquaternium-13, polyquatemium-14, polyquaternium-15, polyquatemium-39, polyquatemium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

If the compositions of the instant invention are intended for use in the dyeing of keratin fibers, and in particular human hair, they generally contain at least one oxidation dyestuff precursor and/or one direct dyestuff, in addition to the unsaturated quaternary ammonium compounds. They also can contain any other adjuvant normally used in this type of composition.

The pH of the dyeing compositions is generally 7 to 11 and can be adjusted to the desired value by adding an alkalizing agent.

The compositions according to this invention also can be used for waving or straightening the hair. In this case, the composition generally contains, in addition to these unsaturated quaternary ammonium compounds, one or more reducing agents and, if appropriate, other adjuvants normally used in this type of composition; such compositions are intended for use conjointly with a neutralizing composition.

In a preferred aspect of this invention, the keratin substrate is skin.

In another preferred aspect, the keratin substrate is hair.

In another preferred aspect, the substrate is a textile fiber material.

Suitable textile fibers for treatment using the UV-absorbing composition of this invention include natural or synthetic fibers or mixtures thereof. Examples of natural fibers include vegetable fibers such as cotton, viscose, flax, rayon, linen, and the like and animal fibers such as wool, mohair, cashmere, angora, silk, and the like. Synthetic fibers include polyester, polyamide and polyacrylonitrile fibers.

In another preferred aspect of this invention, the substrate is plastic.

The foregoing may be better understood by reference to the following Examples, which are presented for purposes of illustration and are not intended to limit the scope of this invention.

EXAMPLE 1

Preparation of 4-methacrylamidosalicylic acid (4-MASA)

In a 5 L flask, 4-aminosalicylic acid (250 g, Aldrich Chemical Co., Milwaukee, Wis.) is dissolved in acetone (2 L) under a nitrogen atmosphere with the aid of mechanical stirring and methacrylic anhydride (375 g, Aldrich) is added dropwise at ambient temperature over 1 hour. After stirring for 16 hours, the volume of acetone is reduced to 1.0 L by vacuum distillation. The crude solid product, which precipitates from solution, is collected by vacuum filtration. The product is washed with 500 mL of 5:1 water:methanol and then stirred for 30 minutes in 1 L of 5:1 water:methanol. The solid is isolated by vacuum filtration and air-dried overnight to yield 295 g of 4-MASA as a tan solid.

EXAMPLE 2

Preparation of N-[3-(dimethylamino)propyl]methacrylamide-N-(3-bromopropyl)phthalimide quaternary salt (DMAPMA.PQ).

A 500 ml flask is charged with isopropanol (200 mL), MEHQ (methylhydroquinone, 0.5 g), N-(3-bromopropyl) phthalimide (53.6 g, 0.2 mole) and DMAPMA (N-[3-(dimethylamino)propyl]methacrylamide, 37.5 g, 0.22 mole). The mixture is heated at reflux for 12 hours. The solution is then cooled down and the majority of the solvent was removed by vacuum distillation. The resulting viscous liquid is put into freezer overnight. The resulting precipitate is dried and collected to provide the title compound in near quantitative yield.

EXAMPLE 2a

A 1000 ml flask is charged with N-(3-bromopropyl) phthalimide, 78.2 g, 0.292 mole), DMAPMA (55.8 g, 0.324 mole), MEHQ (0.5 g) and water (511 g). The mixture is heated at reflux for 12 hours. The resulting DMAPMA.PQ is collected as an aqueous solution.

EXAMPLE 3

Preparation of N-[3-(dimethylamino)propyl]methacrylamide 1-chloromethylnaphthalene quaternary salt (DMAPMA.MNQ).

A 100 ml flask is charged with 1-chloromethyl naphthalene (7.06 g, 40 mmol), DMAPMA (7.48 g, 44 mmol), MEHQ (0.1 g) and acetone (50 ml). The mixture is heated at reflux for 4 hours. The solvent is then removed under vacuum and the resulting gooey DMAPMA.MNQ solidifies upon standing at room temperature.

EXAMPLE 3a

A 100 ml flask is charged with 1-chloromethyl naphthalene (8.83 g, 50 mmol), DMAPMA (8.9 g, 52.5 mmol), MEHQ (0.1 g) and water (69.2 g). The mixture is heated at 60° C. for 4 hours to provide DMAPMA.MNQ as an aqueous solution.

EXAMPLE 4

Preparation of 5 mole percent N-[3-(dimethylamino)propyl]methacrylamide-N-(3-bromopropyl) phthalimide quaternary salt/47.5 mole percent diallyldimethylammonium chloride/47.5 mole percent acrylamide polymer (DMAPMA-PQ/DADMAC/ AcAm)

Diallyldimethylammonium chloride (64.3% solution, 73.87 g), acrylamide (49.3% solution, 96.35 g), distilled water (322.70 g), and N-[3-(dimethylaminopropyl)]methacrylamide N-3-(bromopropyl)phthalimide quaternary salt (5 g) are added to a 1L Erlenmyer flask. Versene (0.05 g) is added and the pH is adjusted to about 6.4 with 50% aqueous sodium hydroxide (0.2 g). The solution is stirred and heated to 57° C. using a hot plate. The solution is then added to a 1L vacuum sealed glass-lined dewar flask and nitrogen purged at approximately 1.5 L/min for 30 minutes. A solution of ammonium persulfate (0.2 g) in distilled water (1.5 g) and a solution (0.33 g) of sodium metabisulfite (0.76 g) and copper sulfate pentahydrate (0.125 g) in distilled water (99.125 g) are then added to the covered dewar flask through syringes. Once a temperature increase is observed, the nitrogen purge is pulled above the solution and the rate is decreased to 0.4 L/min. The solution is kept in the dewar for one hour after the peak exotherm has been reached.

A 5-neck, 1000 ml resin flask equipped with a mechanical stirrer, side baffles, reflux condenser and nitrogen purge is charged with the above polymer solution (200 g), and distilled water (282.17 g). The solution is then stirred, purged, and heated to 85° C. using a heating mantle. A solution of sodium metabisulfite (2.83 g) in distilled water (14.90 g) is then added to the solution. The temperature is maintained at 85° C. for 2 hours and then dropped to room temperature to provide an aqueous solution of the title polymer.

EXAMPLE 5

Preparation of 4.9 mole percent of N-[3-(dimethylamino)propyl]methacrylamide 1-chloromethylnaphthalene quaternary salt/46.9 mole percent diallyldimethylammonium chloride/48.2 mole percent acrylamide polymer (DMAPMA-MNQ/DADMAC/AcAm) polymer The title polymer is prepared according to the method of Example 4, except substituting N-[3-(dimethylaminopropyl)]methacrylamide-1-(chloromethyl)naphthalene quaternary salt for N-[3-(dimethylaminopropyl)]methacrylamide N-3-(bromopropyl)phthalimide quaternary salt.

Using the methods described in Examples 1–5, the representative polymers listed in Table 1 are prepared. In Table 1, w/w means weight percent, m/m means mole percent, monomer 1 is N-[3-(dimethylamino)propyl]methacrylamide-N-(3-bromopropyl)phthalimide quaternary salt (DMAPMA-PQ), monomer 2 is N-[3-(dimethylamino)propyl]methacrylamide 1-chloromethylnaphthalene quaternary salt (DMAPMA-MNQ), monomer 3 is (3-allyloxy-2-hydroxypropyl)-[3-(2-hydroxybenzoylamino)propyl]-dimethyl ammonium hydroxide, monomer 4 is [(4-carboxy-3-hydroxyphenylcarbamoyl)methyl]-dimethyl-[3-(2-methylacryloylamino)propyl] ammonium hydroxide, monomer 5 is 4-methacrylamidosalicylic acid (4-MASA), AcAM stands for acrylamide, DADMAC stands for diallyldimethylammonium chloride and NVP stands for N-vinylpyrrolidone.

TABLE 1

Representative Polymers

| Polymer | Monomer Composition (weight percent) | Absorption maximum (nm) |
|---|---|---|
| I | Monomer 1/AcAm (20/80 w/w) | 300 |
| II | Monomer 1/AcAm (40/60 w/w) | 300 |
| III | Monomer 2/DADMAC/AcAm (5/47.5/47.5 w/w) | 300 |
| IV | Monomer 2/AcAm (20/80 w/w) | 285 |
| V | Monomer 2/DADMAC/AcAm (20/80 w/w) | |
| VI | Monomer 3/AcAm (20/80 w/w) | 300 |
| VII | Monomer 3/MAPTAC/AA/AcAm (3.2/65.2/5.3/26.3 w/w/w/w) | 300 |
| VIII | Monomer 4/AcAm (20/80 w/w) | 306 |
| IX | Monomer 5/NVP (5/95 m/m) | 306 |

TABLE 1-continued

Representative Polymers

| Polymer | Monomer Composition (weight percent) | Absorption maximum (nm) |
|---|---|---|
| X | Monomer 5/NVP (50/50 m/m) | 306 |
| XI | Monomer 5/NVP/DADMAC (48.7/43.6/7/7 m/m/m) | 306 |

EXAMPLE 6

Representative Shampoo Formulation

A representative shampoo formulation is shown in Table 2. The formulation is prepared by mixing water and sodium laureth sulfate. By adding a mixture of cocamidopropyl betaine and the UV-absorbing polymer to a mixture of water and sodium laureth sulfate, adjusting the pH to about 5 with lactic acid and then adding sodium chloride to achieve the desired viscosity.

TABLE 2

Representative Shampoo Formulation

| Ingredients (INCI) | % w/w |
|---|---|
| Water | Qs to 100 |
| Sodium Laureth Sulfate | 25.0 |
| Cocamidopropyl Betaine | 10.0 |
| Polymeric Sunscreens | 3.0 |
| Lactic Acid | Qs to pH 5.0 |
| Sodium Chloride | 0.35 |
| Fragrance | qs |
| Preservative | qs |

EXAMPLE 7

Representative Clear Conditioner Formulation

A representative conditioner formulation is shown in Table 3. The conditioner is prepared by adding hydroxyethylcellulose to water and mixing well while heating to 50.0° C. Heating is then stopped and the remaining ingredients are added with mixing after each addition. Finally, the pH is adjusted to about 5 with lactic acid.

TABLE 3

Representative Conditioner Formulation

| Ingredients (INCI Name) | % w/w |
|---|---|
| Water | Qs to 100 |
| Hydroxyethylcellulose | 1.0 |
| Myristamine Oxide | 10.0 |
| Propylene Glycol | 4.0 |
| Polymeric Sunscreens | 2.0 |
| Dimethicone Propyl PG-Betaine | 2.0 |
| Cetrimonium Chloride | 2.0 |
| Preservative | qs |
| Fragrance | Qs |
| Lactic Acid | Qs to pH 5.0 |

EXAMPLE 8

Representative Moisturizing Lotion Formulation

A representative moisturizing lotion formulation is shown in Table 4. The lotion is prepared by heat water to 80° C. and slowly sifting the Carbomer into the water. The mixture is stirred at 80° C. until the Carbomer is hydrated. With rapid agitation, the ingredients of Part B are added to the water-carbomer mixture at 80° C. and mixing is continued at 80° C. for 5 minutes. The triethanolamine is then added and mixing is continued for 5 minutes at 80° C. until the mixture is uniform. The mixture is then cooled with continued mixing to 40° C. The UV-absorbing polymer, preservatives and fragrances are added and mixing is continued until the formulation is uniform. The formulation typically has a pH of about 7.0.

TABLE 4

Representative Lotion formulation

| Part | Ingredient (INCI Name) | % w/w |
|---|---|---|
| A- | Water | Qs to 100 |
|  | Carbomer | 0.2 |
| B- | Methyl Glucose Sesquistearate | 0.8 |
|  | PEG-20 Methyl Glucose Sesquistearate | 1.0 |
|  | Cetyl Acetate and Acetylated Lanolin Alcohol | 2.0 |
|  | Cetearyl Alcohol and Ceteareth-20 | 2.0 |
|  | Glyceryl Stearate | 0.5 |
|  | Mineral Oil | 8.0 |
| C- | Triethanolamine | 0.3 |
| D- | Polymeric Sunscreens | 2.0 |
|  | Methyldibromo Glutaronitrile and Dipropylene Glycol | 0.1 |
|  | Fragrance | 0.2 |

Cosmetic formulations containing representative UV-absorbing polymers are tested using the following protocols.

I. Preparation of hair tresses for testing.

The experiments described herein are performed on eight inch long Virgin/Blond hair tresses, available from International Hair Importes and Products Inc., Bellerose, N.Y.

The hair tresses (1.5 g each) are bundled and wetted with water. One gram of sodium laureth sulfate is massaged onto the hair tresses from top to bottom for 1 minute. The hair tresses are then rinsed under 40° C. tap water for 1 minute, soaked in deionized water overnight and air dried.

II. UV Irradiation.

Before UV exposure, the hair tresses are treated with 2% (solid base) polymeric sunscreens aqueous solutions for 5 minutes, then rinsed under deionized water for 30 seconds.

The hair tresses are untied from bundle and spread on sample holders in a single layer. The samples are placed 10 cm away from UV bulbs and exposed to simulated summer-noon sunlight in the Q-Panel Accelerated Weathering Tester at 45° C. and 30% relative humidity for 400 to 600 hours.

III. Colorimeter measurement.

The hair samples are collected from the UV weathering tester. Standardize the colorimeter (LabScan XE, Hunter-Lab). Hunter tristimulus L, a, b values are measured by the use of a Hunter Colorimeter LabScan XE instrument. The reported data, in terms of total color difference, $\Delta E = \sqrt{(9\Delta l^2 + \Delta a^2 + \Delta b^2)}$ and chromaticity difference $\Delta C = \sqrt{(\Delta a^2 + \Delta b^2)}$ between unexposed and exposed sections of a hair tress under UV irradiation are the average of measurements performed at several positions. The index of coloration is calculated as $CI = \Delta E / \Delta C$ IV. Dry hair combing.

Hair combing is conducted on the DiaStron Miniature Tensile Tester MTT 160 (DiaStron Limited., Andover Hampshire, England). The hair tresses after UV exposure are attached to the DiaStron. The tresses are combed through once on the front with the end of the comb. The tresses then will not be handled other than to place on the comb for each run. The combing data collected for each treated hair tress is statistically analyzed using the JMP® program (SAS Institute Inc., Cary, N.C.). The mean Peak Force (gmf) for each replicate are grouped by treatment and analyzed via ANOVA analysis.

V. Wet hair combing.

The treated hair tresses are immersed in deionized water for 5 minutes. The excess water is removed with gloved hand. The tresses are detangled with the wide end of the comb 5 times and then combed 5 times on both sides with the narrow end of the comb. The hair tresses are attached to the DiaStron Miniature Tensile Tester MTT 160 (DiaStron Limited., Andover Hampshire, England), and the combing data is collected for each hair tress and statistically analyzed using the JMP® program (SAS Institute Inc., Cary, N.C.) The mean Peak Force (gmf) for each replicate are grouped by treatment and analyzed via ANOVA analysis.

EXAMPLE 9

Demonstration of Hair Coloration Deduction

In order to demonstrate the effectiveness of the UV-absorbing polymers in reducing hair coloration after UV exposure, quantitative changes in total color and chromacity difference between exposed and unexposed hair tresses and between tresses treated with a representative UV-absorbing polymer of this invention and tresses treated with a comparative product prepared using cinnamidopropyltrimonium chloride (Comparative Sunscreen A) are measured. The results are shown in Table 5.

In Table 5, in polymeric sunscreen 1, the UV-absorbing monomer is DMAPMA.PQ.

TABLE 5

Measurement of Coloration Index

| Colorimeter Reading | L | a | b | $\Delta E$ | $\Delta C$ | $\Delta E/\Delta C$, CI |
|---|---|---|---|---|---|---|
| Unexposed | 40.4 | 6.1 | 16.5 |  |  |  |
| Untreated | 44.6 | 6.6 | 20.3 | 13.3 | 3.8 | 3.5 |
| Polymeric Sunscreen 1 | 41.7 | 6.9 | 19.2 | 4.8 | 2.9 | 1.7 |
| Comparative Sunscreen A | 43.4 | 6.6 | 19.5 | 9.6 | 3.0 | 3.2 |

As shown in Table 5, polymeric sunscreens prepared using UV-absorbing polymers of this invention show a lower Coloration Index (CI) than Comparative Sunscreen A and also have a much lower total color difference ($\Delta E$) than the untreated hair sample. The results indicate that the polymeric sunscreens of this invention provide superior protection of hair from changing color after UV exposure.

EXAMPLE 10

Dry Hair Combing Results

The combing force for exposed and unexposed hair tresses and hair tresses treated with a representative UV-absorbing polymer of this invention and tresses treated with a comparative product prepared using cinnamidopropyltrimonium chloride (Comparative Sunscreen A) are measured using the dry combing procedure described above. The results are shown in Table 6.

TABLE 6

| Dry Hair Combing | | | | |
| --- | --- | --- | --- | --- |
| | Mean (gmf) | Std Dev | Std Err Mean | Lower 95% | Upper 95% |
| Comparative A | 7.6133 | 1.7358 | 1.0022 | 5.489 | 9.738 |
| Polymeric Sunscreen 1 | 10.6350 | 5.3976 | 1.9084 | 6.589 | 14.681 |
| Untreated | 28.5875 | 14.0293 | 4.9601 | 18.073 | 39.102 |

Excessive exposure under UV, hair shows undesirable changes in hair quality. Dryness, reduced strength, rough surface texture are commonly observed for the sun damaged hair. This hair damage is reflected in the combing test as the higher amount of combing force needed to comb (since the hair has more rough surface). As shown in Table 6, untreated hair tresses require significantly more combing force to comb through than the treated hair tresses. The combing force required for hair tresses treated with a representative UV-absorbing polymer of this invention and tresses treated with Comparative Sunscreen A is comparable.

EXAMPLE 11

Wet Hair Combing Results

The combing force for exposed and unexposed hair tresses and hair tresses treated with a representative UV-absorbing polymer of this invention and hair tresses treated with a comparative product prepared using cinnamidopropyltrimonium chloride (Comparative Sunscreen A) are measured using the wet combing procedure described above. The results are shown in Table 7.

TABLE 7

| Wet Hair Combing | | | | |
| --- | --- | --- | --- | --- |
| | Mean | Std Error | Lower 95% | Upper 95% |
| Comparative A | 239.714 | 29.019 | 178.75 | 300.68 |
| Polymeric Sunscreen 1 | 212.714 | 29.019 | 151.75 | 273.68 |
| Untreated | 370.286 | 29.019 | 309.32 | 431.25 |

As shown in Table 7, untreated hair tresses require a higher amount of wet combing force than the treated hair tresses after hair is exposed under UV, which means that the untreated hair tresses have the most hair damage. The combing force required for hair tresses treated with a representative UV-absorbing polymer of this invention and tresses treated with Comparative Sunscreen A is comparable.

Although this invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

The invention claimed is:

1. A composition for protecting a substrate from the effect of ultraviolet light comprising about 0.1 to about 10 weight percent, based on polymer actives, of one or more water-soluble, cationic, ultraviolet light absorbing polymers, wherein the cationic, ultraviolet light absorbing polymers are prepared by polymerizing one or more vinyl, allyl or acrylic monomers with one or more vinyl or acrylic monomers that absorb ultraviolet light radiation having a wavelength of about 200 to about 420 nm.

2. The composition of claim 1 wherein the ultraviolet light absorbing polymers are composed of:
   about 0.001 to about 60 mole percent of monomer A;
   ii) 0 to about 99.999 mole percent of monomer B;
   iii) 0 to about 99.999 mole percent of monomer C; and
   iv) 0 to about 99.999 mole percent of monomer D,
wherein
   monomer A is selected from the group consisting of vinyl and acrylic monomers that absorb ultraviolet light radiation having a wavelength of about 200 to about 420 nm;
   monomers B and C are selected from the group consisting of acrylic acid and salts thereof, methacrylic acid and salts thereof, maleic acid and salts thereof, maleic anhydride, acrylamide, crotonic acid, acrylamidomethyl propane sulfonic acid and salts thereof; and
   monomer D is selected from the group consisting of acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, triallylamine, acid salts of triallylamine, ethylene glycol dimethacrylate, hydroxymethylacrylate, hydroxyethylacrylate, hydroxypropylacrylate, hydroxypropylnethacrylate, diethylene glycol dimethacrylate, triethylene glycol dimethylacrylate, polyethylene glycol dimethacrylate, glycidyl methacrylate, acrylamidomethyl propane sulfonic acid and the sodium salt thereof, vinyl alcohol, vinyl acetate, and N-vinylpyrrolidone, provided that B, C and D are not the same.

3. The composition of claim 2 wherein the ultraviolet light absorbing polymer has a molecular weight of about 10,000 to about 10,000,000.

4. The composition of claim 2 wherein the ultraviolet light absorbing polymer has a molecular weight of about 200,000 to about 2,000,000.

5. The composition of claim 2 wherein monomer A is selected from the group consisting of

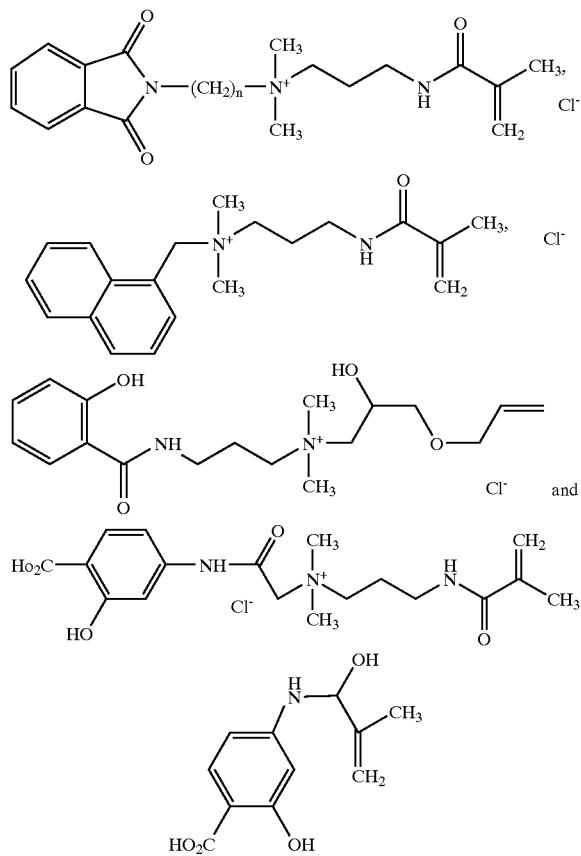

wherein n is 2 or 3.

6. The composition of claim 5 wherein the ultraviolet light absorbing polymer absorbs ultraviolet light radiation having a wavelength of about 290 to about 320 nm.

7. The composition of claim 5 wherein monomers B and C are selected from the group consisting of acrylamide, methacrylic acid, acrylic acid and acrylamidomethyl propane sulfonic acid and monomer D is selected from the group consisting of methacrylamidopropyl trimethylammonium chloride, acrylamidopropyl trimethylammonium chloride, N-vinylpyrrolidinone, dimethylaminopropyl methacrylamide, dimethylaminopropyl acrylamide, diallyldimethylammonium chloride, dimethylaminoethyl acrylate and dimethylaminoethyl methacrylate.

8. The composition of claim 7 comprising about 0.01 to about 50 mole percent of monomer A.

9. The composition of claim 8 wherein monomer B is acrylamide; monomer C is acrylic acid; and monomer D is selected from the group consisting of methacrylamidopropyl trimethylammonium chloride, N-vinylpyrrolidinone and diallyldimethylammonium chloride.

10. The composition of claim 1 further comprising one or more cosmetically acceptable excipients.

11. The composition of claim 10 wherein the excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

12. The composition of claim 11 comprising about 1 to about 3 weight percent, based on polymer actives, of the UV-absorbing polymers.

13. The cosmetically acceptable composition of claim 10 selected from the group consisting of shampoos, aftershaves, sunscreens, hand lotions, skin creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

14. A method of protecting a substrate from the effects of ultraviolet light comprising applying to the substrate an effective ultraviolet light protective amount of the composition of claim 1.

15. The method of claim 14 wherein the substrate is a keratin substrate.

16. The composition of claim 15 wherein the keratin substrate is skin.

17. The method of claim 15 wherein the keratin substrate is hair.

18. The method of claim 14 wherein the substrate is a textile fiber material.

19. The method of claim 14 wherein the substrate is plastic.

* * * * *

UNITED STATES PATENT AND TRADEMARK OFFICE
CERTIFICATE OF CORRECTION

PATENT NO.        : 7,008,618 B1
APPLICATION NO.   : 10/290978
DATED             : March 7, 2006
INVENTOR(S)       : Yin Z. Hessefort et al.

It is certified that error appears in the above-identified patent and that said Letters Patent is hereby corrected as shown below:

Column 24, line 20, should read
--i) about 0.001 to about 60 mole percent of monomer A;--

Signed and Sealed this

Fifth Day of December, 2006

JON W. DUDAS
*Director of the United States Patent and Trademark Office*